(12) United States Patent
Kahne et al.

(10) Patent No.: US 6,388,059 B1
(45) Date of Patent: May 14, 2002

(54) GLYCOSYLATION METHOD

(75) Inventors: Daniel Kahne, Princeton, NJ (US); Jeff Gildersleeve, San Diego, CA (US); Christopher Thompson, Milford, MA (US); Min Ge, Prineton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 09/353,373

(22) Filed: Jul. 14, 1999

Related U.S. Application Data
(60) Provisional application No. 60/092,768, filed on Jul. 14, 1998.

(51) Int. Cl.$^7$ ................................................ C07M 1/00
(52) U.S. Cl. ........................................ 536/18.6; 536/9.1
(58) Field of Search ................................ 536/1.11, 9.1, 536/18.5, 18.6

(56) References Cited

U.S. PATENT DOCUMENTS

| | | | |
|---|---|---|---|
| 5,627,270 A | 5/1997 | Kahne et al. | 536/5 |
| 5,635,612 A | 6/1997 | Kahne | 536/18.5 |
| 5,639,866 A | 6/1997 | Kahne et al. | 536/18.6 |
| 5,700,916 A | 12/1997 | Kahne et al. | 536/1.11 |

OTHER PUBLICATIONS

Gildersleeve et al. J. Am. Chem. Soc. 1998, 120, 5961–5969.*
D. Kahne et al., *J. Am. Chem. Soc.,* 1989, vol. 111, p. 6881.
S. Sato et al., *Tetrahedron Lett.,* 1988, vol. 29, p. 4097.
H. Kunz and A. Harreus, *Liebigs Ann Chem.,* 1982, p. 41.
I.. Fokt et al. *Carbohydr. Res.,* 1991, vol. 222, p. 271.
L. Yan and D. Kahne, *J. Am. Chem. Soc.* 1996, vol. 118, p. 9239.
R. Liang et al., *Science,* 1996, vol. 274, p. 1520.
D. Crich and S. Sun, *J. Org. Chem.* 1997, vol. 62, 1198.

\* cited by examiner

*Primary Examiner*—Elli Peselev
(74) *Attorney, Agent, or Firm*—Woodcock Washburn LLP (57) ABSTRACT

A method for forming a glycosidic linkage by: (a) contacting a glycoside bearing an anomeric sulfoxide group with a compound bearing a free hydroxyl group in the presence of an organic acid anhydride and a scavenger of sulfenyl esters; and (b) allowing a glycosylation reaction to proceed under conditions effective to produce the glycosidic linkage. In a preferred embodiment of the invention, the glycoside bearing an anomeric sulfoxide group is added to a mixture of the other reactants. In another preferred embodiment of the invention, a Lewis acid is also present in the reaction mixture.

This invention is further directed to a method for forming a glycosidic linkage by: (a) forming a solution comprising: a compound bearing a free hydroxyl group, and an organic acid anhydride; (b) adding to the solution a glycoside bearing an anomeric sulfoxide group; and (c) allowing a glycosylation reaction to proceed under conditions effective to produce the glycosidic linkage. In a preferred embodiment of the invention, a Lewis acid is present in the solution.

26 Claims, 1 Drawing Sheet

Figure 1. Low Temperature NMR Data.

GLYCOSYLATION METHOD

RELATED APPLICATIONS

This application claims priority from U.S. Provisional Patent Application No. 60/092,768, filed Jul. 14, 1998 incorporated herein by reference.

BACKGROUND OF THE INVENTION

1. Field of the Invention

The present invention relates to improvements in the sulfoxide glycosylation method for forming glycosidic linkages in solution or on a polymeric support. These improvements increase yield, allow a broader variety of neighboring groups on glycosyl donors and reduce formation of undesired reaction byproducts.

2. Background of the Invention

The sulfoxide glycosylation reaction has been used to make oligosaccharides and other glycoconjugates both in solution and on polymeric supports. See, e.g., D. Kahne et al., J. Am. Chem. Soc., 1989, Vol. 111, page 6881; U.S. Pat. Nos. 5,635,612; 5,627,270; 5,639,866 and 5,700,916. Anomeric sulfoxides can be activated at low temperature with triflic anhydride, leading to rapid glycosylation of nucleophiles, including relatively unreactive nucleophiles. A basic outline of the sulfoxide glycosylation reaction is presented below in Scheme 1.

The sulfoxide oxygen is believed to react with triflic anhydride to form a sulfonium species which ejects phenylsulfenyl triflate to produce an activated species which in turn acts as a glycosyl donor. The activated species reacts with a nucleophile, e.g., the alcohol shown in Scheme 1, to produce a glycoside. Typically, the sulfoxide is referred to as the "glycosyl donor" and the nucleophile as the "glycosyl acceptor."

However, it has been observed that the sulfoxide glycosylation reaction is more complex than is suggested by Scheme 1. In some cases, the activated sulfoxide is extremely reactive at −78° C., and yet is stable at room temperature. See D. Kahne et al. (1989). This behavior suggests that there are other reaction pathways that must be controlled in order to better control the outcome of glycosylation.

As shown in Scheme 1, phenylsulfenyl triflate (PhSOTf) is formed in glycosylation reactions conducted with triflic anhydride. PhSOTf is extremely electrophilic and has the potential to react with a variety of protecting groups, such as allyl ethers and p-methoxybenzyl ethers, and can also cause cleavage of anomeric sulfides. The potential for formation of undesired byproducts increases with the number of functional groups and protecting groups on the glycosyl acceptor.

Glycosylation reactions employing glycosides substituted by halo or other leaving groups at the anomeric position, and alkanoyl esters at the 2-position are known to produce undesired orthoester byproducts. See S. Sato et al., Tetrahedron Lett., 1988, Vol. 29, page 4097; H. Kunz & A. Harreus, Liebigs Ann. Chem., 1982, page 41. Sulfoxide glycosylations are believed to proceed through the same intermediate, and to produce orthoester byproducts when an alkanoyl ester is present at the 2-position.

An improved method for performing sulfoxide glycosylation reactions with reduced levels of byproducts would be useful, especially in preparation of complex glycosylated products such as glycopeptides, in which the diverse functionality often leads to reduced yields of glycosylated product.

SUMMARY OF THE INVENTION

This invention is directed to a method for forming a glycosidic linkage by: (a) contacting a glycoside bearing an anomeric sulfoxide group with a compound bearing a free hydroxyl group in the presence of an organic acid anhydride and a scavenger of sulfenyl esters; and (b) allowing a glycosylation reaction to proceed under conditions effective to produce the glycosidic linkage. In a preferred embodiment of the invention, the glycoside bearing an anomeric sulfoxide group is added to a mixture of the other reactants. In another preferred embodiment of the invention, a Lewis acid is also present in the reaction mixture.

This invention is further directed to a method for forming a glycosidic linkage by: (a) forming a solution comprising: a compound bearing a free hydroxyl group, and an organic acid anhydride; (b) adding to the solution a glycoside bearing an anomeric sulfoxide group; and (c) allowing a glycosylation reaction to proceed under conditions effective to produce the glycosidic linkage. In a preferred embodiment of the invention, a Lewis acid is present in the solution.

DETAILED DESCRIPTION OF THE INVENTION

Definitions

The term "Lewis acid", as used herein, refers to any substance that can accept an electron pair from a base, with the exception of the mineral acids and organic carboxylic acids. The term "DMF" refers to N,N-dimethylformamide; "THF" refers to tetrahydrofuran; "TFA" refers to trifluoroacetic acid; "EtOAc" refers to ethyl acetate; "MeOH" refers to methanol; "MeCN" refers to acetonitrile; "Tf" refers to the trifluoroacetyl group; "DMSO" refers to dimethyl sulfoxide; "DIEA" refers to diisopropylethylamine; "All" in structural formulas refers to the allyl group; "Fmoc" refers to 9-fluorenylmethyloxycarbonyl; "HOBt" refers to 1-hydroxybenzotriazole and "OBt" to the 1-oxybenzotriazolyl group; "PyBOP" refers to benzotriazol-1-yl-oxytripyrrolidine-phosphonium hexafluorophosphate; "Su" refers to the succinimidyl group; "HBTU" refers to O-benzotriazol-1-yl-N,N,N',N'-tetramethyluronium hexafluorophosphate; "aloc" refers to allyloxycarbonyl; and "CBz" refers to benzyloxycarbonyloxy.

The complexity of the glycosylation reaction is illustrated in Scheme 2, which shows the reaction of a sulfoxide (1) with an alcohol (2). Full experimental details of this reaction are provided in Example 2.

MOM = methoxymethyl

Although all of the sulfoxide is consumed at −78° C., only a small amount of the disaccharide product (3) is formed. As the reaction is warmed above −20° C., more product forms. If the reaction is quenched at low temperature, a 23% yield of the desired disaccharide is isolated along with a large quantity of the anomeric sulfenate (4), as shown in Scheme 2.

Figure 1:
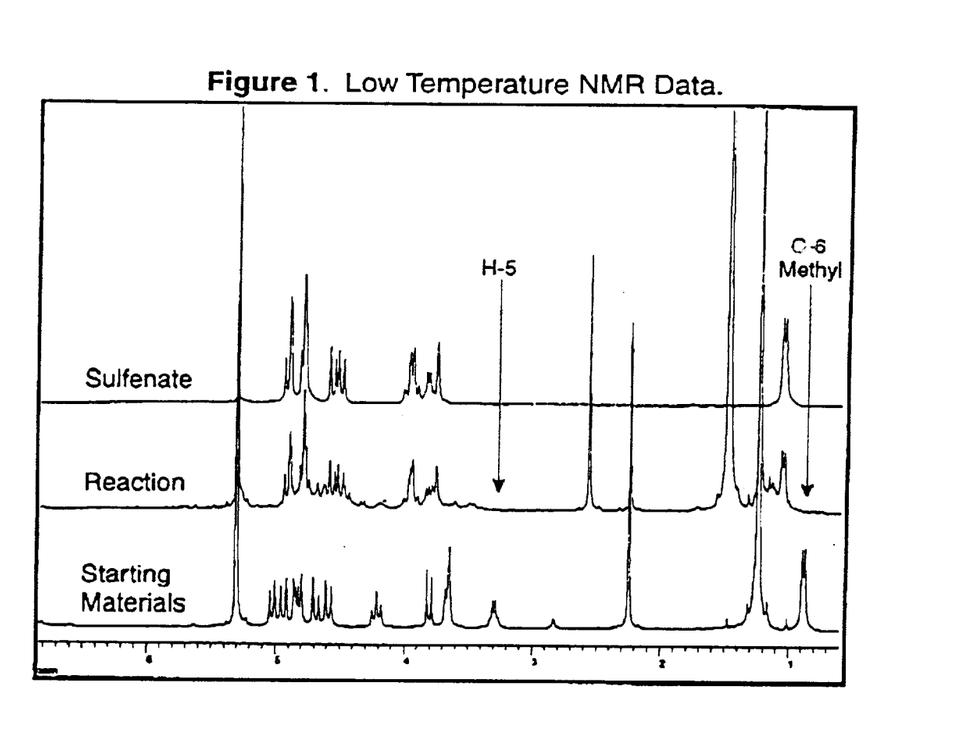
FIG. 1 shows low temperature NMR spectra for the conversion of sulfoxide to sulfenate in the presence of triflic anhydride.

It is believed that anomeric phenylsulfenates decompose rapidly to lactols. See, e.g., I Fokt et al., Carbohydr. Res., 1991, Vol. 222, page 271. Although some of the anomeric sulfenate (4) formed in the reaction shown in Scheme 2 probably decomposes to the lactol, a 50% yield of (4) is actually isolated, suggesting that more than 50% of the sulfoxide reactant is converted to a sulfenate. Clearly, the mechanism leading to formation of the anomeric sulfenate byproduct must be suppressed to obtain high yield and prevent formation of the undesired byproduct. Without being bound by theory, it is believed that anomeric sulfenates are formed from reaction of anomeric sulfoxides in the presence of catalytic amounts of triflic anhydride. Addition of 0.34 equivalents of triflic anhydride to anomeric sulfoxide (1) in the presence of 2,6-di-tert-butyl-4-methylpyridine at −78° C. results in disappearance of all of the sulfoxide, with the anomeric sulfenate being the major species in the reaction mixture, as shown in the $^1$H NMR spectra presented in FIG. 1. Typically, the process for glycosylation using anomeric sulfoxides is performed by mixing the anomeric sulfoxide, the nucleophile and the base, and then adding triflic anhydride. The results shown in FIG. 1 indicate that, even at −78° C., conversion of sulfoxide in the presence of triflic anhydride to the undesired anomeric sulfenate byproduct will compete with glycosylation of the nucleophile to produce the desired glycoside product.

Formation of the undesired anomeric sulfenate byproduct from treatment of an anomeric sulfoxide with a catalytic amount of triflic anhydride is observed in a variety of structurally dissimilar anomeric sulfoxides. Table 1 shows the results obtained from contacting the anomeric sulfoxides listed therein with triflic anhydride and raising the temperature as necessary to induce reaction of the anomeric sulfoxide. Detailed descriptions of these experiments are provided in Examples 4–9. In five of six experiments, an anomeric sulfenate byproduct was formed. The fact that these products do not always form, together with the fact that the temperature required to convert the anomeric sulfoxide to the corresponding sulfenate varies greatly, suggests that there are significant differences in the kinetic accessibility of different anomeric sulfenates. Unfortunately, very little is known about the relative rates of the reactions leading to the desired and undesired products, except that they appear to depend on the structures of the starting sulfoxide and alcohol. Thus it is difficult to predict whether anomeric sulfenate formation will present a problem in any given glycosylation reaction, and it is difficult to control anomeric sulfenate formation by making structural modifications.

TABLE 1

Catalytic Conversion of Sulfoxides.

| Entry | Sulfoxide | Temperature | Yield (α:β)[a] |
|---|---|---|---|
| 1) | (structure 1) | −78° C. | 25% Sulfenate 4<br>65% Lactol |
| 2) | (structure 5) | −78° C. | 71% Sulfenates (6a:6b = 13:1)<br>21% Lactol |

TABLE 1-continued

Catalytic Conversion of Sulfoxides.

| Entry | Sulfoxide | Temperature | Yield (α:β)[a] |
|---|---|---|---|
| 3) |  7 | −78 to −60° C. |  81% 8 |
| 4) |  9 | −78 to −60° C. | 15% Sulfenate 10 (all α) 66% Lactol |
| 5) |  11 | −78° C. | 78% Sulfenates (12a:12b = 1:1) 10% Lactol |
| 6) |  13 | −78 to −25° C. | 15% Sulfenate 14[b] 61% Lactol | a. Yields and α:β are based on purified compounds.
b. It appears that two sulfenates are formed in equal amounts (based on analysis of mass spec., crude NMR, and TLC). Only one of the compounds (14) was stable enough to isolate and characterize. The stereochemistry of 14 was not assigned.

In one embodiment of the present invention, an inverse order of addition is employed to minimize formation of anomeric sulfenates. In conventional glycosylation reactions, an organic acid anhydride is added to a mixture of a glycoside bearing an anomeric sulfoxide group (glycosyl donor), and a compound bearing a free hydroxyl group (glycosyl acceptor). In the present invention, the inverse addition comprises adding the glycosyl donor to the other components. This order of addition avoids extended the contact between the donor and the organic acid anhydride which appears to promote conversion of anomeric sulfoxides to anomeric sulfenates.

Optionally, a non-nucleophilic mild base is added to the mixture of glycosyl acceptor and organic acid anhydride. Suitable non-nucleophilic mild bases include, but are not limited to, porphyrins, 2,6-dialkylanilines, acetamides, 2,6-dialkylpyridines and co-solvents such as ethyl acetate or ethers. The preferred base is 2,6-di-tert-butyl-4-methylpyridine. These bases are useful regardless of the order of addition when acid-sensitive groups are present on the glycosyl donor or acceptor; the base scavenges any hydrogen ion formed in the reaction from reaction of the organic acid anhydride with trace water or released in glycosylation of alcohols. However, when the glycosyl acceptor bears unprotected and very acidic phenolic hydroxyl groups which are not the intended sites of glycosylation, a base is not added because it would cause deprotonation and subsequent glycosylation of the phenolic hydroxyls.

Electrophilic sulfenyl esters, including phenylsulfenyl triflate (PhSOTf), which are normal byproducts of the sulfoxide glycosylation reaction (see Scheme 1), are detrimental to a variety of protecting groups and other functional groups that may be present in sulfoxide glycosylation reactions. In an embodiment of this invention, a scavenger is added to the reaction mixture to react with electrophilic sulfenyl esters. A useful scavenger should react selectively with the sulfenyl ester in the presence of other electrophiles, including the activating agent (i.e., an organic acid anhydride) and the activated glycosyl intermediates, and should also react faster with the sulfenyl ester than the glycosyl acceptor to prevent formation of undesired byproducts from the acceptor. Further, the reaction product formed between the scavenger and the sulfenyl ester should not react with the nucleophilic glycosyl acceptor. Alkenes are generally good scavengers for electrophilic sulfenyl esters. Preferred alkenes are those which are soluble in the reaction solvents at low temperatures, e.g., at −78° C., including norbornylene and 4-allyl-1,2-dimethoxybenzene. Use of alkenes as scavengers is particularly beneficial when inverse addition is employed; it is believed that when the sulfoxide is added to a mixture of glycosyl acceptor and acid anhydride, the sulfenyl ester is not consumed in triflation of the sulfoxide and therefore has extended contact with the acceptor.

The sulfoxide is activated by contacting it with an organic acid anhydride which will react with the sulfoxide. The organic acid anhydride may be an anhydride of a sulfonic acid, of two different sulfonic acids or of a sulfonic acid and a carboxylic acid. The preferred organic acid anhydride is trifluoromethanesulfonic anhydride (triflic anhydride). In sulfoxide glycosylation reactions employing a scavenger of PhSOTf, catalytic activation of the sulfoxide will not be effective. At least about one equivalent of organic acid anhydride, based on the sulfoxide, must be used. Typically, the amount of scavenger added is from about 1 to about 10 equivalents, based on the sulfoxide. Preferably, the amount of scavenger added is from about 5 to about 10 equivalents.

In a preferred embodiment of this invention, a Lewis acid is added to the reaction mixture. A Lewis acid may be used as the sole modification to the sulfoxide glycosylation reaction, or in combination with an inverse order of addition, use of an alkene as a scavenger, or both. Typically, the amount of Lewis acid added ranges from about 1 to about 20 equivalents, based on sulfoxide, and preferably the amount is from about 5 to about 10 equivalents, based on sulfoxide. The preferred Lewis acid is $BF_3$, most preferably as the complex with diethyl ether, $BF_3.Et_2O$. Addition of a Lewis acid improves yield, especially in cases where amide groups are present in the glycosyl acceptor, e.g., in peptides and glycopeptides, and where acetates are present at the position adjacent to the sulfoxide group in the glycosyl donor. If desired, the Lewis acid can be used in combination with a non-nucleophilic mild base such as 2,6-di-tert-butyl-4-methylpyridine. Typically, the base is added in an amount ranging from about 1 to about 10 equivalents, based on the sulfoxide. Preferably, the base is added in an amount ranging from about 2 to about 4 equivalents. Example 18 illustrates the use of $BF_3.Et_2O$ in glycosylation of a vancomycin pseudoaglycone, a complex system having several amide bonds, with vancosamine, one of the natural sugar residues of vancomycin. Examples 16 and 17 illustrate the preparation of the glycosyl donor and acceptor for this reaction. Further details of the structure of vancomycin and glycosylation reactions thereof, can be found in the copending application of Daniel Kahne, Robert Kerns, Seketsu Fukuzawa, Min Ge and Christopher Thompson, titled "Glycopeptide Antibiotics, Combinatorial Libraries of Glycopeptide Antibiotics and Methods of Producing Same," which is incorporated by reference herein.

The following examples are presented in order to illustrate various aspects of the present invention, but are not intended to limit it.

EXAMPLES

Example 1

Methyl 6-O-benzoyl-2,3-di-O-methoxymethyl-α-D-glucopyranoside (2).

To a stirred solution of methyl 4-O-benzyl-2,3-di-O-methoxymethyl-α-D-glucopyranoside (D. B. Berkowitz et al., J. Org. Chem. 1993, vol. 58, page 6174) (1.1 g, 2.96 mmol) in methylene chloride (10 mL) was added triethylamine (3.4 mL, 24.5 mmol), and benzoyl chloride (1.4 mL, 12.0 mmol). The reaction was stirred at room temperature for approximately 30 min and then diluted with EtOAc (100 mL) and washed with 0.5 N aqueous HCl (100 mL), saturated aqueous $NaHCO_3$ (100 mL), and brine (100 mL). The aqueous layers were reextracted with EtOAc (100 mL) and the organics were combined, dried over $Na_2SO_4$, and then concentrated in vacuo. The crude product was taken up in ethanol (7 mL) and Pd/C-Degussa type (100 mg) was added. The reaction was stirred under an atmosphere of hydrogen for 12 h and then filtered through celite and concentrated in vacuo. The product was purified by flash chromatography (gradient 33% to 50% EtOAc/petroleum ether) to afford 2 (0.70 g, 61%) as a colorless oil: $R_f$=0.25 (40% EtOAc/petroleum ether); $^1$H NMR ($CDCl_3$, 270 MHz) δ 8.06 (d, J=7.2 Hz, 2H), 7.56 (t, J=7.2 Hz, 1H), 7.44 (t, J=7.2 Hz, 2H), 4.84 (d, J=3.6 Hz, 1H), 4.7–4.8 (m, 4H), 4.65 (dd, J=2.3, 11.9 Hz, 1H), 4.57 (dd, J=5.3, 11.9 Hz, 1H), 4.23 (br s, 1H), 3.91 (ddd, J=2.3, 5.3, 9.5 Hz, 1H), 3.71 (dd, J=9.5, 9.5 Hz, 1H), 3.61 (dd, J=3.6, 9.5 Hz, 1H), 3.50 (dd, J=9.5, 9.5 Hz, 1H), 3.46 (s, 3H), 3.45 (s, 3H), 3.39 (s, 3H); $^{13}$C NMR ($CD_3COCD_3$, 67.5 MHz) δ 167.0, 134.2, 131.5, 130.5, 129.7, 100.1, 98.8, 98.1, 81.0, 79.2, 71.4, 70.7, 65.2, 56.1, 55.7, 55.5; HRFABMS calcd for $C_{18}H_{27}O_9$ ($M+H^+$) 387.1655, found 387.1656.

Example 2

Methyl (2,3,4-Tri-O-benzyl-α-L-fucopyranosyl)-(1-4)-6-O-benzoyl-2,3-di-O-methoxymethyl-α-D-glycopyranoside (3).

The combined sulfoxide (1) (L. Yan & D. Kahne, J. Am. Chem. Soc. 1996, vol. 118, page 9239) (127 mg, 0.234 mmol) and 2,6-di-tert-butyl-4-methylpyridine (146 mg, 0.711 mmol) were azeotroped three times with toluene (10 mL). To the residue in methylene chloride (7 mL) was added 4 Å molecular sieves (500 mg), and the resulting suspension was stirred at room temperature for 1 h. The suspension was cooled to −78° C. and a solution of triflic anhydride (20 μL, 0.117 mmol) in methylene chloride (300 μL) was added over 1–2 min. The reaction was warmed to −60° C. and then a solution of the alcohol (2) (40 mg, 0.104 mmol) in methylene chloride (4 mL) was added dropwise via syringe. After 15 min at −60° C., the reaction was filtered into saturated aqueous $NaHCO_3$ (30 mL) and extracted with methylene chloride (3×20 mL). The organic layers were combined, dried over $Na_2SO_4$, and concentrated in vacuo. The products were purified by flash chromatography (gradient 8–70% EtOAc/petroleum ether) to afford the disaccharide (3) (19 mg, 23%), sulfenate (4) (63 mg, 50%), and unreacted alcohol (2) (24 mg, 60%). Disaccharide (3): $R_f$=0.3 (30% EtOAc/petroleum ether); $^1$H NMR ($CDCl_3$, 270 MHz) δ 8.03 (d, J=6.9 Hz, 2H), 7.15–7.65 (m, 18H), 5.03 (d, J=3.6 Hz, 1H), 4.95 (d, J=11.5 Hz, 1H), 4.6–4.9 (m, 11H), 4.52 (dd, J=4.3, 12.2 Hz, 1H), 4.25 (q, J=6.3 Hz, 1H), 4.07 (dd, J=3.6, 10.2 Hz, 1H), 3.8–4.0 (m, 3H), 3.74 (dd, J=9.3, 9.3 Hz, 1H), 3.68 (br s, 1H), 3.53 (dd, J=3.6, 9.3 Hz, 1H), 3.39 (s, 3H), 3.38 (s, 3H), 3.36 (s, 3H), 1.11 (d, J=6.3 Hz, 3H); $^{13}$C NMR ($CD_3COCD_3$, 67.5 MHz) δ 166.6, 140.4, 140.2, 139.8, 130.3, 129.5, 129.2, 129.1, 129.05, 129.0, 128.7, 128.4, 128.3, 128.2, 128.16, 100.0, 99.9, 99.3, 98.4, 80.5, 80.2, 79.3, 79.0, 77.2, 77.1, 75.7, 74.5, 73.0, 69.9, 68.1, 64.7, 56.6, 55.5, 55.3, 17.1; HRFABMS calcd for $C_{45}H_{53}O_{13}$ ($M-H^-$) 801.3486, found 801.3499.

Sulfenate (4): $R_f$=0.4 (10% EtOAc/petroleum ether); $^1$H NMR ($CDCl_3$, 270 MHz) δ 7.15–7.5 (m, 20H), 5.01 (d, J=3.6 Hz, 1H), 4.96 (d, J=11.6 Hz, 1H), 4.87 (d, J=11.6 Hz, 1H), 4.77 (t, J=11.3 Hz, 2H), 4.62 (d, J=11.6 Hz, 2H), 4.07 (dd, J=3.6, 10.2 Hz, 1H), 3.97 (dd, J=2.6, 10.2 Hz, 1H), 3.79 (q, J=6.6 Hz, 1H), 3.65 (m, 1H), 1.03 (d, J=6.6 Hz, 3H); $^{13}$C NMR ($CD_3COCD_3$, 67.5 MHz) δ 142.2, 140.7, 140.6, 140.3, 130.3, 129.7, 129.6, 129.5, 129.3, 129.2, 128.8, 128.7, 125.4, 106.9, 80.2, 79.4, 79.2, 76.3, 74.7, 73.7, 69.3, 29.6; HRDCIMS calcd for $C_{33}H_{38}NO_5S$ ($M+NH_4^+$) 560.2471, found 560.2471.

Example 3

General Procedure for the Catalytic Conversion of Sulfoxides.

The combined sulfoxide (0.20 mmol) and 2,6-di-tert-butyl-4-methylpyridine (0.40 mmol) were azeotroped three times with toluene (10 mL). The residue was taken up in methylene chloride (7 mL) and 4 Å molecular sieves (500 mg) were added. The resulting suspension was stirred at room temperature for 1 h and then cooled to −78° C. 40 μL of a triflic anhydride stock solution (10 μL triflic anhydride in 400 μL of methylene chloride; 40 μL of stock is approximately 0.006 mmol) was added over 1 min via syringe. The reaction was monitored by TLC and warmed if necessary until all of the sulfoxide completely disappeared. The reaction was filtered into saturated aqueous $NaHCO_3$ (30 ML) and extracted with methylene chloride (3×20 mL). The organic layers were combined, dried over $Na_2SO_4$, and concentrated in vacuo. The products were purified by flash chromatography.

Example 4
Catalytic Conversion of 2,3,4-Tri-O-benzyl-1-phenylsulfinyl-α-L-fucopyranose (1).

Catalytic conversion of sulfoxide (1) afforded 25% of 2,3,4-tri-O-benzyl-1-(phenylsulfenyl)-α-L-fulcopyranose (4) and 65% of an anomeric mixture of lactols.

Example 5
Synthesis and Catalytic Conversion of 2,3,4-Tri-O-benzyl-1-(2,6-dimethylphenylsulfinyl)-β-L-fulcopyranoside (5a,b).

To a solution of 1,2,3,4tetra-O-acetyl-L-fucopyranoside (7.8 g, 23.5 mmol) in methylene chloride (60 mL) was added 2,6-dimethylthiophenol (4.7 mL, 35.3 mmol). The reaction was cooled to at −72° C. and boron trifluoride etherate (5.8 mL, 47.2 mmol) was added dropwise via syringe. The reaction was warmed slowly to 0° C. and stirred at 0° C. overnight. Saturated aqueous $NaHCO_3$ (50 mL) was added and the reaction was stirred vigorously for 15 min. The organic layer was then separated, dried over $Na_2SO_4$, and concentrated in vacuo. The product was purified by flash chromatography (10% acetone/petroleum ether) to afford 2,6-dimethylphenyl 2,3,4-tri-O-acetyl-1-thio-β-L-fucopyranoside (7.7 g, 80%): $R_f$=0.25 (15% acetone/petroleum ether); $^1$H NMR ($CDCl_3$, 270 MHz) δ 7.13 (m, 3H), 5.31 (dd, J=10.2, 10.2 Hz, 1H), 5.22 (d, J=3.6 Hz, 1H), 4.99 (dd, J=3.6, 10.2 Hz, 1H), 4.38 (d, J=10.2 Hz, 1H), 3.62 (q, J=6.6 Hz, 1H), 2.55 (s, 6H), 2.20 (s, 3H), 2.13 (s, 3H), 1.99 (s, 3H), 1.14 (d, J=6.6 Hz, 3H); $^{13}$C NMR ($CD_3COCD_3$, 67.5 MHz) δ 171.6, 170.7, 170.5, 145.4, 132.9, 130.7, 129.7, 89.7, 73.8, 73.5, 71.9, 69.4, 23.2, 21.4, 21.2, 17.1; HRFABMS calcd for $C_{20}H_{26}O_7SNa$ (M+Na$^+$) 433.1297, found 433.1313.

To the above sulfide (3.0 g, 7.32 mmol) in methanol (25 mL) was added sodium methoxide (100 mg). The resulting solution was stirred at room temperature overnight and then neutralized with Amberlite IR-120® (plus) acidic resin. The resin was filtered and rinsed several times with methanol (3×30 mL). The combined filtrate was concentrated in vacuo and used without further purification.

To the crude tetraol (~7.32 mmol) in THF (20 mL) was added benzyl bromide (5.2 mL, 43.9 mmol). The reaction was cooled to 0° C. and NaH (925 mg of 95% dispersion, 36.6 mmol) was added. Tetrabutylammonium iodide (1.0 g) was added and DMF (10 mL) and the reaction was allowed to warm to room temperature. The reaction was quenched by slow addition of $H_2O$ (10 mL) and then diluted with EtOAc (100 mL) and extracted with $H_2O$ (50 mL), brine (50 mL), dried over $Na_2SO_4$, and concentrated in vacuo. The product was purified by flash chromatography (50% methylene chloride/petroleum ether) to afford 2,6-dimethylphenyl 2,3,4-tri-O-benzyl-1-thio-β-L-fucopyranoside (3.0 g, 74%): $R_f$=0.3 (5% EtOAc/petroleum ether); $^1$H NMR ($CDCl_3$, 270 MHz) δ 7.0–7.5 (m, 18H), 5.06 (d, J=10.5 Hz, 1H), 4.98 (d, J=11.9 Hz, 1H), 4.88 (d, J=10.5 Hz, 1H), 4.72 (m, 3H), 4.27 (d, J=9.6 Hz, 1H), 3.87 (dd, J=9.6, 9.6 Hz, 1H), 3.57 (d, J=2.6 Hz, 1H), 3.50 (dd, J=2.6, 9.6 Hz, 1H), 3.26 (q, J=6.3 Hz, 1H), 2.56 (s, 6H), 1.07 (d, J=6.3 Hz, 3H); $^{13}$C NMR ($CD_3COCD_3$, 67.5 MHz) δ 145.0, 140.3, 140.0, 139.9, 133.3, 129.7, 129.2, 129.0, 128.95, 128.9, 128.8, 128.5, 128.3, 128.25, 128.2, 90.9, 85.5, 79.5, 78.0, 76.2, 75.7, 74.7, 73.2, 22.9, 17.5; HRFABMS calcd for $C_{35}H_{37}O_4S$ (M−H$^−$) 553.2413, found 553.2438.

To the above sulfide (500 mg, 0.903 mmol) in methylene chloride (10 mL) at −42° C. was added 3-chloroperoxybenzoic acid (272 mg of 65% dispersion, 1.02 mmol). The reaction was allowed to warm to −5° C. and then cooled to −30° C. and dimethyl sulfide (100 μL) was added. The reaction was diluted with methylene chloride (50 mL) and extracted with saturated aqueous $NaHCO_3$ (50 mL). The organic layer was dried over $Na_2SO_4$ and concentrated in vacuo. The products were purified by flash chromatography (5:4:1 methylene chloride:petroleum ether:EtOAc) to afford a mixture of 2,3,4-tri-O-benzyl-1-(2,6-dimethylphenylsulfinyl)-β-L-fucopyranosides (5) (430 mg, 84%). More polar diastereomer: $R_f$=0.3 (5:4:1 methylene chloride:petroleum ether:EtOAc); $^1$H NMR ($CDCl_3$, 270 MHz) δ 7.1–7.5 (m, 16H), 7.01 (d, J=7.6 Hz, 2H), 5.09 (d, J=9.9 Hz, 1H), 4.99 (d, J=11.9 Hz, 1H), 4.87 (d, J=9.9 Hz, 1H), 4.70 (m, 3H), 4.35 (dd, J=9.1, 9.1 Hz, 1H), 3.69 (dd, J=2.4, 9.1 Hz, 1H), 3.59 (d, J=2.4 Hz, 1H), 3.44 (q, J=6.3 Hz, 1H), 2.57 (s, 6H), 1.01 (d, J=6.3 Hz, 3H); $^{13}$C NMR ($CD_3COCD_3$, 67.5 MHz) δ 140.9, 140.7, 140.5, 140.2, 132.1, 130.8, 129.7, 129.6, 129.5, 129.3, 129.1, 129.0, 128.9, 128.7, 128.6, 94.4, 85.8, 78.3, 77.7, 76.0, 75.9, 75.7, 73.4, 20.6, 17.7; HRDCIMS calcd for $C_{35}H_{42}NO_5S$ (M+NH$_4^+$) 588.2784, found 588.2804. Less polar diastereomer: $R_f$=0.35 (5:4:1 methylene chloride:petroleum ether:EtOAc); $^1$H NMR ($CDCl_3$, 270 MHz) δ 7.1–7.5 (m, 18H), 6.98 (d, J=7.6 Hz, 2H), 5.0 (m, 3H), 4.75 (m, 3H), 4.53 (dd, J=9.6, 9.6 Hz, 1H), 4.06 (d, J=9.6 Hz, 1H), 3.68 (dd, J=2.6, 9.6 Hz, 1H), 3.62 (m, 1H), 3.42 (q, J=6.3 Hz, 1H), 2.55 (s, 6H), 1.10 (d, J=6.3 Hz, 3H); $^{13}$C NMR ($CD_3COCD_3$, 67.5 MHz) δ 140.8, 140.3, 140.2, 137.2, 131.6, 131.1, 129.8, 129.6, 129.5, 129.3, 129.2, 129.1, 129.0, 128.9, 128.8, 94.4, 85.8, 78.2, 76.9, 76.5, 76.2, 75.1, 73.4, 20.4, 17.8; HRDCIMS calcd for $C_{35}H_{39}O_5S$ (M+H$^+$) 571.2518, found 571.2528.

Catalytic conversion of sulfoxide (5) afforded 66% of 2,3,4-tri-O-benzyl-1-(2,6-dimethylphenylsulfenyl)-α-L-fucopyranose (6a), 5% of 2,3,4-tri-O-benzyl-1-(2,6-dimethylphenylsulfenyl)-β-L-fucopyranose (6b), and 21% of an anomeric mixture of lactols. Sulfenate (6a): $R_f$=0.5 (10% EtOAc/petroleum ether); $^1$H NMR ($CDCl_3$, 270 MHz) δ 7.0–7.5 (m, 18H), 4.95 (d, J=3.6 Hz, 1H), 4.89 (d, J=11.5 Hz, 1H), 4.83 (d, J=11.7 Hz, 1H), 4.69 (d, J=11.7 Hz, 1H), 4.66 (d, J=12.2 Hz, 1H), 4.57 (d, J=11.5 Hz, 1H), 4.52 (d, J=12.2 Hz, 1H), 3.96 (dd, J=3.6, 10.2 Hz, 1H), 3.80 (dd, J=2.4, 10.2 Hz, 1H), 3.50 (d, J=2.4 Hz, 1H), 3.26 (q, J=6.6 Hz, 1H), 2.57 (s, 6H), 0.62 (d, J=6.6 Hz, 3H); $^{13}$C NMR ($CD_2Cl_2$, 67.5 MHz) δ 143.4, 139.5, 139.4, 139.2, 136.9, 131.4, 128.9, 128.8, 128.7, 128.65, 128.6, 128.3, 128.0, 104.7, 79.2, 78.8, 77.5, 75.5, 73.5, 73.4, 68.0, 22.0, 16.3; HRDCIMS calcd for $C_{35}H_{42}NO_5S$ (M+NH$_4^+$) 588.2784, found 588.2795. Sulfenate (6b): $R_f$=0.4 (10% EtOAc/petroleum ether); $^1$H NMR ($CDCl_3$, 270 MHz) δ 7.0–7.5 (m, 18H), 4.95 (d, J=11.5 Hz, 1H), 4.65 (m, 5H), 4.39 (d, J=7.6 Hz, 1H), 3.76 (dd, J=7.6, 9.5 Hz, 1H), 3.47 (m, 3H), 2.59 (s, 6H), 1.19 (d, J=6.3 Hz, 3H); $^{13}$C NMR ($CD_3COCD_3$, 67.5 MHz) δ 144.5, 140.8, 140.5, 137.5, 132.7, 129.6, 129.5, 129.4, 129.3, 129.1, 129.0, 128.7, 128.6, 109.2, 84.0, 81.0, 78.4, 76.2, 75,9, 73.9, 72.3, 22.6, 17.6; HRDCIMS calcd for $C_{35}H_{42}NO_5S$ (M+NH$_4^+$) 588.2784, found 588.2783.

Example 6
Catalytic Conversion of 2,3,4-tri-O-pivaloyl-1-(phenylsulfinyl)-α-L-fucopyranose (7).

Catalytic conversion of sulfoxide (7) (R. Liang et al., Science, 1996, vol. 274, page 1520) afforded 81% of 1,3,4-tri-O-pivaloyl-α-L-fucopyranose (8): $R_f$=0.33 (20% EtOAc/petroleum ether); $^1$H NMR (CDCl$_3$, 270 MHz) δ 6.24 (d, J=3.6 Hz, 1H), 5.30 (d, J=3.3 Hz, 1H), 5.24 (dd, J=3.3, 10.6 Hz, 1H), 4.25 (m, 2H), 1.88 (d, J=8.2 Hz, 1H), 1.28 (s, 18H), 1.20 (s, 9H), 1.13 (d, J=6.6 Hz, 3H); $^{13}$C NMR (CD$_3$COCD$_3$, 67.5 MHz) δ 178.4, 178.2, 177.7, 93.8, 72.4, 72.0, 68.7, 67.0, 40.4, 40.2, 39.9, 28.1, 28.0, 27.9, 16.9; HRFABMS calcd for $C_{21}H_{36}O_8Na$ (M+Na$^+$) 439.2308, found 439.2319.

Example 7
Catalytic Conversion of 2,3,4,6-tetra-O-benzyl-1-(phenylsulfinyl)-α-D-glucopyranose (9).

Catalytic conversion of sulfoxide (9) (Kahne et al. 1989) afforded 15% of 2,3,4,6-tetra-O-benzyl-1-(phenylsulfenyl)-α-D-glucopyranose (10) and 66% of an anomeric mixture of lactols. Sulfenate (10): $R_f$0.5 (10% EtOAc/petroleum ether); $^1$H NMR (CDCl$_3$, 270 MHz) δ 7.55 (m, 2H), 7.2–7.4 (m, 21H), 7.13 (m, 2H), 5.00 (d, J=3.6 Hz, 1H), 4.97 (d, J=12.2 Hz, 1H), 4.82 (d, J=10.9 Hz, 1H), 4.80 (d, J=10.9 Hz, 1H), 4.70 (d, J=11.9 Hz, 1H), 4.59 (m, 2H), 4.46 (d, J=10.9 Hz, 1H), 4.43 (d, J=12.2 Hz, 1H), 4.00 (dd, J=9.2, 9.2 Hz, 1H), 4.7 (m, 3H), 3.57 (dd, J=3.6, 9.2 Hz, 1H), 3.39 (m, 1H); $^{13}$C NMR (CD$_3$COCD$_3$, 67.5 MHz) δ 141.6, 140.6, 140.2, 140.1, 139.9, 132.4, 130.4, 129.7, 129.65, 129.6, 129.3, 129.2, 129.0, 128.8, 128.7, 128.6, 126.4, 105.9, 82.8, 82.1, 79.1, 76.5, 76.1, 74.45, 74.4, 73.4, 70.0; HRFABMS calcd for $C_{40}H_{40}O_6NaS$ (M+Na$^+$) 671.2443, found 671.2456.

Example 8
Synthesis and Catalytic Conversion of 2,3,4,6-Tetra-O-methyl-1-(phenylsulfinyl)-β-D-galactopyranoside (11).

To a solution of phenyl 1-thio-β-D-galactopyranoside (Ferrier, R. J.; Furneaux, R. H., Methods in Carbohydrate Chemistry; Academic Press: New York, 1980; Vol. VII) (4.0 g, 14.7 mmol) in DMF (80 mL) at 0° C. was add NaH (3.0 g of a 95% dispersion, 118 mmol). Methyl iodide (5.5 mL, 88 mmol) was added via syringe over 5 min. The reaction was warmed to room temperature and stirred overnight. Methanol (5 mL) was added slowly over 15 min and the reaction was diluted with EtOAc (100 mL) and extracted with H$_2$O (100 mL), brine (100 mL), dried over Na$_2$SO$_4$, and concentrated in vacuo. The product was purified by flash chromatography (25% EtOAc/petroleum ether) to afford of phenyl 2,3,4,5-tetra-O-methyl-1-thio-β-D-galactopyranoside (4.0 g, 83%): $R_f$=0.3 (33% EtOAc/petroleum ether); $^1$H NMR (CDCl$_3$, 270 MHz) δ 7.55 (d, J=7.6 Hz, 2H), 7.25 (m, 3H), 4.50 (d, J=9.4 Hz, 1H), 3.70 (d, J=3.0 Hz, 1H), 3.59 (s, 3H), 3.56 (s, 3H), 3.45–3.65 (m, 3H), 3.53 (s, 3H), 3.41 (dd, J=9.4, 9.4 Hz, 1H), 3.37 (s3H), 3.20 (dd, J=3.0, 9.4 Hz, 1H); $^{13}$C NMR (CD$_3$COCD$_3$, 67.5 MHz) δ 136.6, 131.9, 130.2, 128.0, 88.4, 87.3, 80.6, 78.1, 76.7, 72.4, 61.7, 61.5, 59.7, 58.7; HRFABMS calcd for $C_{16}H_{24}O_5NaS$ (M+Na$^+$) 351.1242, found 351.1239.

To the above sulfide (353 mg, 1.08 mmol) in methylene chloride (10 mL) at −42° C. was added 3-chloroperoxybenzoic acid (314 mg of 65% dispersion, 1.18 mmol). The reaction was warmed slowly to −10° C. and then cooled to −30° C. and dimethylsulfide (100 μL) was added. The reaction mixture was diluted with methylene chloride (30 mL) and extracted with saturated aqueous NaHCO$_3$ (30 mL), dried over Na$_2$SO$_4$, and concentrated in vacuo. The products were purified by flash chromatography (25% acetone/petroleum ether) to afford a mixture of sulfoxides (11) (319 mg, 86%). Less polar diastereomer: $R_f$=0.25 (25% acetone/petroleum ether); $^1$H NMR (CDCl$_3$, 270 MHz) δ 7.68 (m, 2H), 7.49 (m, 3H), 4.19 (d, J=8.9 Hz, 1H), 3.84 (dd, J=8.9, 8.9 Hz, 1H), 3.65 (d, J=2.6 Hz, 1H), 3.56 (m, 3H), 3.50 (s, 3H), 3.48 (s, 3H), 3.46 (s, 3H), 3.37 (s, 3H), 3.30 (dd, J=2.6, 8.9 Hz, 1H);). $^{13}$C NMR (CD$_3$COCD$_3$, 67.5 MHz) δ 144.1, 131.5, 129.9, 125.6, 98.5, 87.3, 78.9, 76.1, 75.0, 72.4, 61.6, 60.5, 59.6, 58.3; HRDCIMS calcd for $C_{16}H_{25}O_6S$ (M+H$^+$) 345.1372, found 345.1363. More polar diastereomer: $R_f$=0.22 (25% acetone/petroleum ether); $^1$H NMR (CDCl$_3$, 270 MHz) δ 7.63 (m, 2H), 7.48 (m, 3H), 4.01 (dd, J=9.5, 9.5 Hz, 1H), 3.80 (s, 3H), 3.78 (d, J=9.5 Hz, 1H), 3.71 (d, J=2.6 Hz, 1H), 3.65 (m, 1H), 3.63 (s, 3H), 3.61 (s, 3H), 3.40 (m, 3H), 3.27 (s, 3H); $^{13}$C NMR (CD$_3$COCD$_3$, 67.5 MHz) δ 142.6, 131.7, 130.0, 126.5, 94.8, 87.4, 79.7, 76.6, 76.3, 71.9, 61.8, 61.6, 59.5, 58.6; HRDCIMS calcd for $C_{16}H_{25}O_6S$ (M+H$^+$) 345.1372, found 345.1382.

Catalytic conversion of sulfoxide (11) afforded 39% of 2,3,4,6-tetra-O-methyl-1-(phenylsulfenyl)-α-D-galactopyranose (12a), 40% of 2,3,4,6-tetra-O-methyl-1-(phenylsulfenyl)-β-D-galactopyranose (12b), and 10% of an anomeric mixture of lactols. Sulfenate (12a): $R_f$=0.28 (15% acetone/petroleum ether); $^1$H NMR (CDCl$_3$, 270 MHz) δ 7.51 (d, J=7.3 Hz, 2H), 7.38 (t, J=7.3 Hz, 2H), 7.25 (m, 1H), 5.09 (d, J=3.3 Hz, 1H), 3.77 (m, 2H), 3.60 (dd, J=3.3, 8.9 Hz, 1H), 3.55 (s, 3H), 3.52 (s, 3H), 3.47 (m, 2H), 3.43 (s, 3H), 3.34 (s, 3H), 3.24 (dd, J=5.3, 8.9 Hz, 1H); $^{13}$C NMR (CD$_3$COCD$_3$, 67.5 MHz) δ 142.2, 130.4, 128.3, 125.9, 106.8, 81.3, 80.2, 77.5, 72.1, 71.8, 61.9, 59.9, 59.7, 58.8; HRDCIMS calcd for $C_{16}H_{25}O_6S$ (M+H$^+$) 345.1372, found 345.1377.

Sulfenate 12b: $R_f$=0.25 (15% acetone/petroleum ether); $^1$H NMR (CDCl$_3$, 270 MHz) δ 7.40 (m, 4H), 7.20 (m, 1H), 4.41 (d, J=7.9 Hz, 1H), 3.64 (m, 2H), 3.60 (s, 3H), 3.57 (s, 3H), 3.53 (m, 1H), 3.50 (s, 3H), 3.40 (m, 2H), 3.39 (s, 3H), 3.12 (dd, J=3.3, 9.9 Hz, 1H); $^{13}$C NMR (CD$_3$COCD$_3$, 67.5 MHz) δ 142.2, 130.3, 128.1, 125.3, 110.7,85.5, 82.8, 76.4, 75.1, 72.1, 61.7, 61.6, 59.6, 58.9; HRFABMS calcd for $C_{16}H_{24}O_6NaS$ (M+Na$^+$) 367.1191, found 367.1205.

Example 9
Catalytic Conversion of 2,3-di-O-benzyl-4,6-benzylidene-1-(phenylsulfinyl)-α-D-mannopyranose (13).

Catalytic conversion of sulfoxide (13) (Crich, D.; Sun, S., J. Org. Chem. 1997, vol. 62, 1198) afforded 15% of 2,3-di-O-benzyl-4,6-O-benzylidene-1-(phenylsulfenyl)-β-D-mannopyranose (14) and 61% of an anomeric mixture of lactols. Sulfenate (14): $R_f$=0.33 (15% acetone/petroleum ether); $^1$H NMR (CDCl$_3$, 270 MHz) δ 7.2–7.6 (m, 20H), 5.60 (s, 1H), 4.96 (d, J=12.0 Hz, 1H), 4.88 (d, J=12.0 Hz, 1H), 4.73 (d, J=12.2 Hz, 1H), 4.59 (d, J=12.2 Hz, 1H), 4.57 (s, 1H), 4.34 (dd, J=4.9, 10.5 Hz, 1H), 4.21 (dd, J=9.6, 9.6 Hz, 1H), 3.92 (m, 2H), 3.57 (dd, J=3.0, 9.6 Hz, 1H), 3.34 (ddd, J=4.9, 9.6, 9.6 Hz, 1H); $^{13}$C NMR (CD$_3$COCD$_3$, 67.5 MHz) δ 141.8, 140.6, 140.5, 139.7, 130.5, 130.0, 129.6, 129.5, 129.4, 128.8, 128.7, 128.6, 127.7, 125.9, 108.8, 102.7, 79.8, 79.7, 79.0, 76.6, 73.4, 69.6, 69.2; HRFABMS calcd for $C_{33}H_{33}O_6S$ (M+H$^+$) 557.1998, found 557.1999.

Example 10
Glycosylation Using Sulfenate (4) as the Glycosyl Donor.

Sulfenate (4) (34 mg, 0.063 mmol), alcohol (2) (25 mg, 0.065 mmol), and 2,6-di-tert-butyl-4-methylpyridine (91 mg, 0.44 mmol) were azeotroped three times with toluene (10 mL). Methylene chloride (5 mL) was added followed by 4 Å molecular sieves (500 mg). The resulting suspension was stirred at room temperature for 1 h and then cooled to −78° C. A solution of triflic anhydride (21 μL, 0.125 mmol) in methylene chloride (350 μL) was added over 1–2 min. The reaction was warmed slowly and monitored by TLC for the disappearance of sulfenate (4) and the formation of disaccharide (3). After 15 min at 0° C., the reaction was filtered into saturated aqueous NaHCO$_3$ (30 mL) and extracted with methylene chloride (3×20 mL). The organic layers were combined, dried over Na$_2$SO$_4$, and concentrated in vacuo. The product was purified by flash chromatography (33% EtOAc/petroleum ether) to afford disaccharide (3) (26 mg, 50%).

Example 11
Comparison of Glycosylation Procedures.

(a) Preactivation: The combined sulfoxide (1) (82 mg, 0.151 mmol) and 2,6-di-tert-butyl-4-methylpyridine (224 mg, 1.09 mmol) were azeotroped three times with toluene (10 mL). To the residue in methylene chloride (5 mL) was added 4 Å molecular sieves (500 mg), and the resulting suspension was stirred at room temperature for 1 h. The suspension was cooled to −78° C. and a solution of triflic anhydride (46 μL, 0.272 mmol) in methylene chloride (350 μL) was added over 1–2 min. A solution of alcohol (2) (26 mg, 0.067 mmol) in methylene chloride (3 mL) was added dropwise via syringe. The reaction was warmed to −50° C. and, after 15 min at −50° C., the reaction was filtered into saturated aqueous NaHCO$_3$ (30 mL) and extracted with methylene chloride (3×20 mL). The organic layers were combined, dried over Na$_2$SO$_4$, and concentrated in vacuo. The product was purified by flash chromatography (33% EtOAc/petroleum ether) to afford disaccharide (3) (14 mg, 26%).

(b) Premix. The combined sulfoxide (1) (80 mg, 0.148 mmol), alcohol (2) (25 mg, 0.065 mmol) and 2,6-di-tert-butyl-4-methylpyridine (223 mg, 1.09 mmol) were azeotroped three times with toluene (10 mL). To the residue in methylene chloride (8 mL) was added 4 Å molecular sieves (500 mg), and the resulting suspension was stirred at room temperature for 1 h. The suspension was cooled to −78° C. and a solution of triflic anhydride (45 μL, 0.267 mmol) in methylene chloride (350 μL) was added over 1–2 min. The reaction was warmed to −50° C. and, after 15 min at −50° C., the reaction was filtered into saturated aqueous NaHCO$_3$ (30 mL) and extracted with methylene chloride (3×20 mL). The organic layers were combined, dried over Na$_2$SO$_4$, and concentrated in vacuo. The product was purified by flash chromatography (33% EtOAc/petroleum ether) to afford disaccharide (3) (20 mg, 38%).

(c) Inverse Addition. The combined alcohol (2) (25 mg, 0.065 mmol) and 2,6-di-tert-butyl-4-methylpyridine (220 mg, 1.07 mmol) were azeotroped three times with toluene (10 mL). To the residue in methylene chloride (5 mL) was added 4 Å molecular sieves (500 mg), and the resulting suspension was stirred at room temperature for 1 h. The suspension was cooled to −78° C. and a solution of triflic anhydride (45 μL, 0.267 mmol) in methylene chloride (350 μL) was added over 1–2 min. A solution of sulfoxide (2) (80 mg, 0.148 mmol) in methylene chloride (3 mL) was added via syringe over 10–15 min. The reaction was warmed to −50° C. and, after 15 min at −50° C., the reaction was filtered into saturated aqueous NaHCO$_3$ (30 mL) and extracted with methylene chloride (3×20 mL). The organic layers were combined, dried over Na$_2$SO$_4$, and concentrated in vacuo. The product was purified by flash chromatography (33% EtOAc/petroleum ether) to afford disaccharide (3) (34 mg, 65%).

Scheme 2:
Synthesis of Monomers

Example 12
2,6-Dichlorophenyl 2-deoxy-3-O-(4-methoxybenzyl)-1-thio-α-L-fucopyranoside.

A combined solution of 2,6-dichlorophenyl 2-deoxy-1-thio-α-L-fucopyranoside (604 mg, 1.96 mmol) and dibutyltin oxide (536 mg, 2.16 mmol) in benzene (25 mL) was fitted with a Dean-Stark apparatus and refluxed overnight. The reaction was cooled to room temperature and 4-methoxybenzyl chloride (1.06 mL, 7.82 mmol) and tetrabutylammonium bromide (635 mg, 1.97 mmol) were added. The reaction was refluxed for 3.5 h, cooled to room temperature and concentrated in vacuo. The crude reaction mixture was purified by silica gel chromatography (25% ethyl acetate/petroleum ether) to afford (15) (833 mg, 99%): R$_f$=0.30 (33% EtOAc/petroleum ether); $^1$H NMR (CDCL$_3$, 270 MHz) δ 7.38 (d, J=8.2 Hz, 2H), 7.25 (m, 3H), 6.90 (d, J=8.2 Hz, 2H), 5.76 (d, J=5.6 Hz, 1H), 4.56 (s, 2H), 4.46 (q, J=6.6 Hz, 1H), 3.90 (m, 1H), 3.84 (m, 1H), 3.82 (s, 3H), 2.33 (ddd, J=5.6, 7.9, 11.9 Hz, 1H), 2.15 (m, 2H), 1.22 (d, J=6.6 Hz, 3H);

Example 13
Phenyl 4-acetyl-2-deoxy-3-O-(4-methoxybenzyl)-1-thio-α-L-fucopyranoside.

To a solution of phenyl 2-deoxy-3-O-(4-methoxybenzyl)-1-thio-α-L-fucopyranoside (752 mg, 2.09 mmol) in methylene chloride (10 mL) was added triethylamine (1.2 mL, 8.4 mmol), acetic anhydride (0.40 mL, 4.2 mmol), and dimethylaminopyridine (~5 mg). The reaction was stirred at room temperature for 5 h and then poured into saturated NaHCO3 (40 mL) and extracted three times with methylene chloride (3–40 mL). The combined organic layers were dried over sodium sulfate and concentrated in vacuo. The crude mixture was purified by silica gel chromatography to afford (16) (700 mg, 83%) as a white solid: R$_f$=0.35 (20% EtOAc/petroleum ether); $^1$H NMR (CDCL$_3$, 270 MHz) δ

7.43 (d, J=8.5 Hz, 2H), 7.27 (m, 5H), 6.88 (d, J=8.5 Hz, 2H), 5.72 (d, J=5.6 Hz, 1H), 5.37 (d, J=2.8 Hz, 1H), 4.65 (d, J=10.9 Hz, 1H), 4.45 (q, J=6.6 Hz, 1H), 4.38 (d, J=10.9 Hz, 1H), 3.89 (ddd, J=2.8, 4.6, 12.5 Hz, 1H), 3.81 (s, 3H), 2.39 (ddd, J=5.6, 12.5, 12.7 Hz, 1H), 2.17 (2, 3H), 2.08 (dd, J=4.6, 12.7 Hz, 1H), 1.17 (d, J=6.6 Hz, 3H); $^{13}$C NMR (CD$_3$COCD$_3$, 67.5 MHz) δ 171.4, 160.8, 138.8, 132.6, 132.0, 130.8, 130.4, 128.4, 115.1, 85.6, 73.1, 70.8, 70.3, 67.4, 56.1, 33.4, 21.4, 17.6;

Example 14

4-O-Acetyl-2-deoxy-3-O-(4-methoxybenzyl)-1-(phenylsulfinyl)-α-L-fucopyranoside.

The sulfide (16) (298 mg, 0.74 mmol) was taken up in methylene chloride (10 mL) and solid sodium bicarbonate (200 mg, 2.38 mmol) was added. The reaction was cooled to −42° C. and 3-chloroperbenzoic acid (248 mg dispersion, 0.79 mmol) was added. The reaction was warmed slowly until the sulfide had completely reacted. The reaction was cooled to −42° C. and quenched with dimethyl sulfide (3 drops). The reaction was poured into saturated NaHCO$_3$ (30 mL) and extracted three times with methylene chloride (3×30 mL). The combined organic layers were dried over sodium sulfate and concentrated in vacuo. The crude mixture was purified by silica column chromatography (50% ethyl acetate/petroleum ether) to afford the sulfoxide (17) (255 mg, 82%) as a white solid: $R_f$=0.25 (33% EtOAc/petroleum ether); $^1$H NMR (CDCl$_3$, 270 MHz) δ 7.55 (m, 5H), 7.27 (m, 2H), 6.88 (d, J=8.6 Hz, 2H), 5.41 (d, J=2.0 Hz, 1H), 4.66 (d, J=10.6 Hz, 1H), 4.57 (d, J=5.6 Hz, 1H), 4.42 (d, J=10.6 Hz, 1H), 4.30 (q, J=6.3 Hz, 1H), 4.20 (ddd, J=2.0, 5.0, 12.2 Hz, 1H), 3.81 (s, 3H), 2.56 (dd, J=5.0, 14.5 Hz, 1H), 2.15 (m, 4H), 1.20 (d, J=6.3 Hz, 3H); $^{13}$C NMR (CD$_3$COCD$_3$, 67.5 MHz) δ 171.3, 160.7, 144.9, 132.3, 31.8, 130.7, 130.4, 125.7, 114.9, 97.2, 72.6, 72.2, 70.8, 69.5, 56.0, 25.2, 21.2, 17.8;

Scheme 3:
Glycosylation Reaction

Example 15

2,6-Dichlorophenyl [4-O-acetyl-2-deoxy-3-O-(4-methoxybenzyl)-α-L-fucopyranoside]-(1-4)-2-deoxy-3-O-(4-methoxybenzyl)-1-thio-α-L-fucopyranoside.

(a) Inverse Addition.

The combined alcohol (15) (38 mg, 0.089 mmol) and 2,6-di-tert-butyl-4-methylpyridine (83 mg, 0.40 mmol) were azeotroped three times with toluene (10 mL). To the residue in methylene chloride (4 mL) was added 4 Å molecular sieves (500 mg), and the resulting suspension was stirred at room temperature for 1 h. The suspension was cooled to −78° C. and a solution of triflic anhydride (23 μL, 0.136 mmol) in methylene chloride (350 μL) was added over 1–2 min. A solution of sulfoxide (17) (57 mg, 0.136 mmol) in methylene chloride (2 mL) was added via syringe over 10–15 min. After 15 min at −78° C., the reaction was quenched with diethylamine (100 μL), filtered into saturated aqueous NaHCO$_3$ (30 mL), and extracted with methylene chloride (3×20 mL). The organic layers were combined, dried over Na$_2$SO$_4$, and concentrated in vacuo. The product was purified by flash chromatography (33% EtOAc/petroleum ether) to afford disaccharide (18) (26 mg, 40%): $R_f$=0.35 (33% EtOAc/petroleum ether); $^1$H NMR (CDCl$_3$, 270 MHz) δ 7.39 (d, J=7.8 Hz, 2H), 7.21 (m, 5H), 6.89 (d, J=7.8 Hz, 2H), 6.83 (d, J=8.9 Hz, 2H), 5.80 (d, J=5.3 Hz, 1H), 5.25 (d, J=2.0 Hz, 1H), 5.04 (m, 1H), 4.58 (m, 3H), 4.36 (m, 3H), 3.88 (m, 3H), 3.82 (s, 3H), 3.78 (s, 3H), 2.38 (ddd, J=5.3, 12.5, 12.8 Hz, 1H), 2.16 (m, 1H), 2.12 (s, 3H), 1.98 (m, 2H), 1.13 (d, J=6.6 Hz, 3H), 0.88 (d, J=6.6 Hz, 3H); $^{13}$C NMR (CD$_3$COCD$_3$, 67.5 MHz) δ 171.5, 160.8, 160.7, 142.7, 133.4, 132.4, 132.2, 132.1, 130.8, 130.4, 130.3, 115.0, 114.9, 100.5, 86.5, 76.2, 74.6, 72.6, 71.0, 70.9, 70.8, 70.7, 66.5, 56.1, 56.0, 32.7, 32.6, 21.4, 18.1, 17.7;

(b) Inverse Addition with norborylene.

The combined alcohol (15) (47 mg, 0.110 mmol) and 2,6-di-tert-butyl-4-methylpyridine (138 mg, 0.672 mmol) were azeotroped three times with toluene (10 mL). To the residue in methylene chloride (4.5 mL) was added 4 Å molecular sieves (500 mg), norbonylene (158 mg, 1.68 mmol), and the resulting suspension was stirred at room temperature for 1 h. The suspension was cooled to −78° C. and a solution of triflic anhydride (28 μL, 0.165 mmol) in methylene chloride (350 μL) was added over 1–2 min. A solution of sulfoxide (17) (69 mg, 0.165 mmol) in methylene chloride (2.5 mL) was added via syringe over 10–15 min. After 15 min at −78° C., the reaction was quenched with diethylamine (100 μL), filtered into saturated aqueous NaHCO$_3$ (30 mL), and extracted with methylene chloride (3×20 mL). The organic layers were combined, dried over Na$_2$SO$_4$, and concentrated in vacuo. The product was purified by flash chromatography (33% EtOAc/petroleum ether) to afford disaccharide (18) (60 mg, 76%).

note: with 2 eq of norbornylene the yield was 69%.

(c) Inverse Addition with allyldimethoxybenzene.

The combined alcohol (15) (42 mg, 0.098 mmol), allyldimethoxybenzene (250 μL, 1.45 mmol), and 2,6-di-tert-butyl-4-methylpyridine (87 mg, 0.42 mmol) were azeotroped three times with toluene (10 mL). To the residue in methylene chloride (4.5 mL) was added 4 Å molecular sieves (500 mg), and the resulting suspension was stirred at room temperature for 1 h. The suspension was cooled to −78° C. and a solution of triflic anhydride (25 μL, 0.148 mmol) in methylene chloride (350 μL) was added over 1–2 min. A solution of sulfoxide (17) (62 mg, 0.148 mmol) in methylene chloride (2.5 mL) was added via syringe over 10–15 min. After 15 min at −78° C., the reaction was quenched with diethylamine (100 μL), filtered into saturated aqueous NaHCO$_3$ (30 mL), and extracted with methylene chloride (3×20 mL). The organic layers were combined, dried over Na$_2$SO$_4$, and concentrated in vacuo. The product was purified by flash chromatography (33% EtOAc/petroleum ether) to afford disaccharide (18) (58 mg, 82%).

note: with 3 eq of allyldimethoxybenzene the yield was 77%.

Example 16
Allyl-dialoc-tri-OAll peracetate vancomycin pseudoaglycone (21).

a) Allyl dialoc-tri-O-allyl vancomycin (19).

All-dialoc vancomycin (753 mg, 0.455 mmol) is taken in 5 mL DMF. Ground $Cs_2CO_3$ (750 mg, 2.30 mmol) is added to the reaction solution. The suspension is stirred under high vacuum for 30 minutes. Then allyl bromide (400 L, 2.36 mmol) is added. TLC at 6 hours shows completed reaction. The suspension is precipitated in 100 mL water, centrifuged. The white solid is collected and loaded to a silica gel column (30 mm×12 cm) and eluted with gradient from $CHCl_3$ to 5% $MeOH/CHCl_3$ to give 660 mg (82%) of compound (19) as white solid. $R_f$=0.6 (20% $MeOH/CHCl_3$). Mass Spec. $[M+Na]^+$, 1776; $[M-V]^+$, 1550, $[M-V-G]$, 1387.

b) Allyl-dialoc-tri-O-allyl peracetate vancomycin (20).

Allyl dialoc-tri-O-allyl vancomycin (19) (100 mg, 0.0563 mmol) is dissolved in 5 mL $CH_2Cl_2$. Pyridine (164 L, 2.027 mmol) is added followed by 2 mg DMAP. The reaction solution turns clear. $Ac_2O$ (96 mL, 1.013 mmol) is added. After 5 hours, TLC shows completed reaction. The reaction is quenched with 1 mL methanol and then all solvents are removed. The residue is loaded to a silica gel column (30 mm×12 cm) and eluted with a gradient of 0% to 5% $MeOH/CHCl_3$ to give 104 mg (91%) of compound (20) as white solid. $R_f$=0.3 (5% $MeOH/CHCl_3$). Mass Spec. $[M+Na]^+$ 2028.

c) Allyl-dialoc-tri-OAll peracetate vancomycin pseudoaglycone (21).

Allyl-dialoc-tri-OAll peracetate vancomycin (20) (238 mg, 0.117mmol) is azeotroped with toluene 3 times and then dissolved in 8 mL $CH_2Cl_2$. PhSH (120 L, 1.173 mmol) is added followed by $BF_3.Et_2O$(431 L, 3.51 mmol). TLC at 2 hours shows completed reaction. The reaction is quenched by 1 mL of DIEA and all solvents are removed. The residue is loaded to a silica gel column (30 mm×12 cm) and eluted with a gradient of 0 to 5% $MeOH/CHCl_3$ to give 144 mg (70%) of compound (21) as white solid. $R_f$=0.3 (5% $MeOH/CHCl_3$). Mass Spec. $[M+Na]^+$ 2028.

Example 17
Vancosamine N-CBz-C-6-O-acetyl sulfoxide (26).

a) N,N'-bis-Cbz, vancomycin (22).

To a solution of vancomycin.HCl (1.76 g, 1.19 mmol) dissolved in 8.5 mL water and diluted with 10 mL acetone is added 3 mL water containing $NaHCO_3$ (210 mg, 2.5 mmol). To the stirred suspension is added 20 mL acetone, 15 mL water and N-(benzyloxycarbonyloxy)succinimide (1.2 g, 4.8 mmol) as a solution in 3 mL acetone. After 15 h. the clear solution is evaporated to dryness under reduced pressure with toluene azeotrope. The solid is dissolved in 15 mL DMF and precipitated by addition to 120 mL tetrahydrofuran. The suspension is centrifuged and the supernatant containing reagents decanted. The solid is then suspended in 120 mL acetone, mixed vigorously, centrifuged, and the supernatant decanted. This acetone wash of the solid is performed 3 times to remove all reagents. The white solid is dried under reduced pressure affording (22) (1.9 g, 95%) that is used without further manipulation. TLC: $R_f$=0.33 (chloroform-methanol-water; 6:4:1). LRESI-MS calc for $C_{82}H_{87}N_9O_{28}Cl_2$ 1715.5; $[M+Na]^+$=1739; $[M\text{-vancosamine}+H]^+$=1440; $[M\text{-disaccharide}+H]^+$=1277 b) Vancosamine N-CBz methoxide (23).

Crude vancomycin BisCBz (22) (3.414 g, 1.99 mmol) is dissolved in 18 mL methanol and 2.7 mL 10N HCl aqueous solution is added. A white precipitate is formed during reaction. After 2 hours, TLC shows completed reaction. All the solvents are removed and the residue is precipitated in 300 mL acetone. The acetone layer is collected and concentrated to give a thick oil. This oil is loaded onto a silica gel column (40 mm×14 cm) and eluted with 60% ETOAc/PE to give 303 mg (75%) of compound (23) as clear oil. (:=2:1) $R_f$=0.2 (40% ETOAc/PE)

c) Vancosamine N-CBz C-4-O-acetyl methoxide (24).

The compound (23) (49 mg, 0.159 mmol) is dissolved in 2 mL $CH_2Cl_2$. DMAP (0.2 mg) is added to the reaction followed by pyridine (13 L, 12.6 mmol) and acetic anhydride (15 L, 16.23 mmol). After 12 hours, TLC shows completed reaction. The reaction is quenched by 0.5 mL methanol and all the solvents are removed. The residue is loaded to a silica gel column (20 mm×14 cm) and eluted with 30% ETOAc/PE to give 53 mg (95%) of compound (24) as clear oil. (:=2:1). anomer: $R_f$=0.4 (40% EtOAc/PE); $^1$H NMR ($CDCl_3$, 300 MHz) 7.35 (m, 5H), 5.25–4.90 (m, 3H), 4.79 (d, J=6.5 Hz, H-1, 1H), 4.74 (bs, H-4, 1H), 4.10 (m, H-5, 1H), 3.34 (s, $OCH_3$, 3H), 2.10 (s, $COCH_3$, 3H), 2.00–1.88 (m, H-2, H-2', 2H), 1.73 (s, $CH_3$, 3H), 1.14 (d, J=6.4 Hz, $CH_3$, 3H). anomer: $R_f$=0.3 (40% EtOAc/PE); $^1$H NMR ($CDCl_3$, 300 MHz) 7.35 (m, 5H), 5.10 (d, J=12.0 Hz, 1H), 5.09 (s, 1H), 4.95 (d, J=12.0 Hz, 1H), 4.73 (bs, H-4, 1H), 4.55 (d, J=12.0 Hz, H-1, 1H), 3.84 (m, H-5, 1H), 3.50 (s, $OCH_3$, 3H), 2.07 (s, $COCH_3$, 3H), 2.00–1.70 (m, H-2, H-2', 2H), 1.64 (s, $CH_3$, 3H), 1.20 (d, J=6.4 Hz, $CH_3$, 3H).

d) Vancosamine N-CBz C4-O-acetyl sulfide (25).

The compound (24) (144 mg, 0.410 mmol) is azeotroped with toluene 3 times and then dissolved in 4 mL $CH_2Cl_2$. PhSH (84 L, 0.82 mmol) is added followed by $BF_3OEt_2$ (100 L, 0.82 mmol). TLC at 15 minutes shows completed reaction. The reaction is quenched by 20 mL saturated $NaHCO_3$ aqueous solution. The $CH_2Cl_2$ layer is separated and the aqueous layer is further extracted with $CH_2Cl_2$ (20 mL×3). The $CH_2Cl_2$ layers are combined and dried over anhydrous sodium sulfate, filtered, concentrated to give a clear oil. This oil is loaded to a silica gel column (30 mm×14 cm) and eluted with 20% ETOAc/PE to give 125 mg (71%) compound (25) as white solid. Rf=0.7 (40% EtOAc/PE) (:=3:1) anomer: $^1$H NMR ($CDCl_3$, 500 Mhz) 7.47–7.24 (m, 10H), 5.58 (dd, J=2.8, 6.7 Hz, H-1, 1H), 5.10 (d, J=12.2 Hz, 1H), 5.00–4.97 (m, 3H), 4.90 (s, H-4, 1H), 4.51 (m, H-5, 1H), 2.55 (dd, J=6.7, 14.0 Hz, H-2, 1H), 2.23 (d, J=14.0 Hz, H-2', 1H), 2.09 (s, $COCH_3$, 3H), 1.77 (s, $CH_3$, 3H), 1.16 (d, J=6.4 Hz, $CH_3$, 3H); $^{13}$C NMR ($CDCl_3$, 500 MHz) 170.94, 154.69, 136.60, 136.02, 131.20, 129.06, 128.71, 128.46, 128.35, 127.31, 83.12, 74.01, 66.61, 64.44, 53.66, 37.35, 24.11, 20.87, 17.13; anomer: $^1$H NMR ($CDCl_3$, 500 MHz) 7.47–7.24 (m, 10H), 5.58 (dd, J=2.8, 6.7 Hz, H-1, 1H), 5.10 (d, J=12.2 Hz, 1H), 5.00–4.97 (m, 3H), 4.90 (s, H-4, 1H), 4.51 (m, H-5, 1H), 2.55 (dd, J=6.7, 14.0 Hz, H-2, 1H), 2.23 (d, J=14.0 Hz, H-2', 1H), 2.09 (s, $COCH_3$, 3H), 1.77 (s, $CH_3$, 3H), 1.16 (d, J=6.4 Hz, $CH_3$, 3H); $^{13}$C NMR ($CDCl_3$, 500 MHz) 170.94, 154.69, 136.60, 136.02, 131.20, 129.06, 128.71, 128.46, 128.35, 127.31, 83.12, 74.01, 66.61, 64.44, 53.66, 37.35, 24.11, 20.87, 17.13.

e) Vancosamine N-CBz C4-O-acetyl sulfoxide (26).

The vancosamine sulfide (25) (18 mg, 0.0433 mmol) is dissolved in 1.5 mL $CH_2Cl_2$ and cooled to −78° C. mCPBA is added and the reaction is slowly warmed up to −20° C. in 1 hour. TLC shows completed reaction. The reaction is quenched by 100 mL dimethyl sulfide. The reaction is extracted with 5 mL saturated $NaHCO_3$ aqueous solution. The aqueous layer is further extracted with $CH_2Cl_2$ (5 mL×3). The $CH_2Cl_2$ layers are combined and dried over anhydrous sodium sulfate, filtered, concentrated to a clear oil. This oil is loaded onto a silica gel column (20 mm×8 cm) and eluted with 60% ETOAc/PE to give 19 mg (95%) compound (26) as white solid. $R_f$=0.15 (40% EtOAc/PE).

Example 18

Regeneration of Vancomycin from (21)

a) Glycosylation of (21) with (26) to give (20).

The compound (21) (22.7 mg, 0.0127 mmol) is azeotroped and dissolved in 1 mL $CH_2Cl_2$ and cooled to −78° C. $BF_3.Et_2O$ (2 L, 0.0168 mmol) is added followed by triflic anhydride (4 L, 0.0247 mmol). Then the sulfoxide (26) (22 mg, 0.0494 mmol) in 0.5 mL $CH_2Cl_2$ is added to the reaction vessel dropwise over 1 minute. TLC shows all sulfoxide is activated after addition. The reaction is slowly warmed up to −25° C. in 1.5 hour and then quenched with 100 mL methanol and 100 mL DIEA. All the solvents are removed and the residue is loaded to a silica gel column (10 mm×5 cm) and eluted with a gradient of 0 to 5% $MeOH/CHCl_3$ to give 17 mg of white solid. This white solid is purified by reverse-phase HPLC using a PHENOMENEX LUNA $C_{18}$ column (21.2×250 mm), 5 m particle, eluting with a 30 min. linear gradient of 80% acetonitrile/0.1% acetic acid in water to 100% acetonitrile/0.1% acetic acid; flow rate of 8 mL/min. and UV detection at 285 nm. The fractions containing the pure products are combined and evaporated to give 11 mg (41%) of compound (20) as white solid. $R_f$=0.3 (5% $MeOH/CHCl_3$). Mass Spec. $[M+Na]^+$ 2028.

b) Deprotection of compound (20) to give compound (19).

The glycosylation product (20) (9 mg, 0.00443 mmol) is dissolved in 0.4 mL methanol and 0.2 mL THF. Hydrazine (30 L) is added. The reaction is quenched with 0.2 mL of acetic acid after 4 hours. All solvents are removed and the residue is purified by reverse-phase HPLC using a PHENOMENEX LUNA $C_{18}$ column (21.2×250 mm), 5 m particle, eluting with a 30 min. linear gradient of 80% acetonitrile/0.1% acetic acid in water to 100% acetonitrile/0.1% acetic acid; flow rate of 8 mL/min. and UV detection at 285 nm. The fractions containing the pure products are combined and evaporated to give 5 mg (63%) of compound (19) as white solid. $R_f$=0.3 (5% $MeOH/CHCl_3$). Mass Spec. $[M+Na]^+$ 2028.

c) Deprotection of Compound (19) to give Vancomycin.

Compound (19) (5 mg, 0.00281 mmol) is dissolved in 0.5 mL DMF/0.5 mL acetic acid. A catalytic amount of palladium dichloride-bis-triphenylphosphine is added and the reaction vessel is filled with nitrogen. To this mixture is added, with vigorous stirring, tributyltin hydride in 5 µL portions every 5 minutes until all starting materials and intermediates have disappeared by TLC. The crude reaction mixture is precipitated with 20 mL diethyl ether in a 50 mL centrifuge tube. The mixture is centrifuged and decanted to give a white solid that is vortexed with 20 mL diethyl ether, centrifuged, decanted and dried. The resulting white solid is purified by reverse-phase HPLC using a PHENOMENEX LUNA C18 column (21.2×250 mm), 5 µm particle, eluting with a 40 min. linear gradient of 0.1% trifluoroacetic acid in water to 20% acetonitrile/0.1% trifluoroacetic acid in water; flow rate of 7 mL/min. and ultraviolet (UV) detection at 285 nm. The fractions containing the product are combined, diluted with 10 mL water, organic solvents are evaporated and then the residue is lyophilized to give 3 mg (75%) of vancomycin TFA salt as white solid. $R_f$=0.05 ($CHCl_3:MeOH:H_2O$=3:4:2). Mass Spec. $[M+Na^+]$ 1471.

The preceding examples are intended to describe certain preferred embodiments of the present invention. It should be appreciated, however, that obvious additions and modifications of the invention will be apparent to one skilled in the art. The invention is not limited except as set forth in the claims.

What is claimed is:

1. A method for forming a glycosidic linkage; said method comprising:

(a) contacting a glycoside bearing an anomeric sulfoxide group with a compound bearing a free hydroxyl group in the presence of an organic acid anhydride and a scavenger of sulfenyl esters, said scavenger being an alkene; and (b) allowing a glycosylation reaction to proceed under conditions effective to produce the glycosidic linkage.

2. The method of claim 1 in which the organic acid anhydride is triflic anhydride.

3. The method of claim 2, further comprising addition of a non-nucleophilic mild base.

4. The method of claim 3 in which the non-nucleophilic mild base is 2,6-di-tert-butyl-4-methylpyridine.

5. The method of claim 4 in which the alkene is norbornylene.

6. The method of claim 4 in which the alkene is 4-allyl-1,2-dimethoxybenzene.

7. The method of claim 1 in which the glycoside bearing an anomeric sulfoxide group is added to a mixture comprising: the compound bearing a free hydroxyl group, the organic acid anhydride and the sulfenyl ester scavenger, said scavenger being an alkene.

8. The method of claim 7 in which the organic acid anhydride is triflic anhydride.

9. The method of claim 8, further comprising a non-nucleophilic mild base in the mixture.

10. The method of claim 9 in which the non-nucleophilic mild base is 2,6-di-tert-butyl-4-methylpyridine.

11. The method of claim 10 in which the alkene is norbornylene.

12. The method of claim 10 in which the alkene is 4-allyl-1,2-dimethoxybenzene.

13. The method of claim 1, further comprising addition of a Lewis acid.

14. The method of claim 13 in which the Lewis acid is $BF_3$.

15. The method of claim 14 in which the organic acid anhydride is triflic anhydride.

16. The method of claim 15, further comprising addition of a non-nucleophilic mild base.

17. The method of claim 16 in which the non-nucleophilic mild base is 2,6-di-tert-butyl-4-methylpyridine.

18. A method for forming a glycosidic linkage, said method comprising;

(a) forming a solution comprising: a compound bearing a free hydroxyl group, and an organic acid anhydride;

(b) adding to the solution a glycoside bearing an anomeric sulfoxide group, in which said glycoside is added over a period of time in a manner that provides a higher yield of said glycosidic linkages than a conventional glycosylation reaction; and (c) allowing a glycosylation reaction to proceed under conditions effective to produce the glycosidic linkage.

19. The method of claim 18 in which the organic acid anhydride is triflic anhydride.

20. The method of claim 19, further comprising a non-nucleophilic mild base in the solution.

21. The method of claim 20 in which the non-nucleophilic mild base is 2,6-di-tert-butyl-4-methylpyridine.

22. A method for forming a glycosidic linkage, said method comprising:

(a) forming a solution comprising a compound bearing a free hydroxyl group, a Lewis acid, and an organic acid anhydride;
(b) adding to the solution a glycoside bearing an anomeric sulfoxide group; and
(c) allowing a glycosylation reaction to proceed under conditions effective to produce the glycosidic linkage.

23. The method of claim 22 in which the Lewis acid is $BF_3$.

24. The method of claim 23 in which the organic acid anhydride is triflic anhydride.

25. The method of claim 24, further comprising a non-nucleophilic mild base in the solution.

26. The method of claim 25 in which the non-nucleophilic mild base is 2,6-di-tert-butylpyridine.

* * * * *